US00PP29623P3

(12) United States Plant Patent
Gradziel et al.

(10) Patent No.: US PP29,623 P3
(45) Date of Patent: Aug. 28, 2018

(54) PEACH TREE NAMED 'VILMOS'

(50) Latin Name: *Prunus persica*
Varietal Denomination: Vilmos

(71) Applicant: The Regents of the University of California, Oakland, CA (US)

(72) Inventors: Thomas M. Gradziel, Davis, CA (US); Mary Ann Thorpe, Davis, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 152 days.

(21) Appl. No.: 14/999,841

(22) Filed: Jul. 7, 2016

(65) Prior Publication Data

US 2018/0014444 P1 Jan. 11, 2018

(51) Int. Cl.
*A01H 5/08* (2018.01)
*A01H 6/74* (2018.01)

(52) U.S. Cl.
USPC ..... Plt./197
CPC ..... *A01H 6/7463* (2018.05); *A01H 5/08* (2013.01)

(58) Field of Classification Search
USPC ..... Plt./197
See application file for complete search history.

(56) References Cited

PUBLICATIONS

The Jan. 1, 1999 Test Agreement for Trees (No. 2015-5005) between Richard Zolezzi and The Regents of the University of California, 7 pages.
The Jan. 1, 2004 Test Agreement for Peach Trees (No. 2016-5015) between Richard McPherrin and The Regents of the University of California, 7 pages.
The Apr. 1, 2015 Test Agreement for Trees (No. 2015-5002) between Sierra Gold Nurseries, Inc. and The Regents of the University of California, 7 pages.
The May 1, 2015, Test Agreement for Trees (No. 2015-5003) between Dave Wilson Nursery and The Regents of the University of California, 7 pages.

*Primary Examiner* — Anne Marie Grunberg
(74) *Attorney, Agent, or Firm* — Morrison and Foerster LLP

(57) ABSTRACT

A new peach variety (*Prunus persica*) designated as 'Vilmos' is provided. 'Vilmos' forms attractive, high quality fruit that matures during the commercially important 'Andross' period, and demonstrates a capacity to maintain good on-tree fruit quality for up to 10 days following initial ripening, allowing delayed harvest and economically efficient single harvests. Further, 'Vilmos' fruit exhibits the desirable characteristics of being free from the red staining of the pit area of fruit flesh in addition to having low susceptibility to splitting or cracking of the fruit pit during ripening, while also having other desirable fruit characteristics that are substantially similar to 'Andross'.

5 Drawing Sheets

Latin name: Botanical/commercial classification: *Prunus persica*, new peach cultivar.

Varietal denomination: The varietal denomination of the claimed peach variety is 'Vilmos'.

BACKGROUND OF THE INVENTION

An objective of processing peach breeding programs is to develop new peach varieties that are commercially desirable. In particular, there is a need for the development of new peach varieties that are suitable replacements for the 'Early' maturity season varieties 'Dixon', 'Andross', and 'Klampt' (each non-patented in the United States).

Peach variety 'Dixon' originated in Linden, Calif., by F. A. Dixon, of the Canners League of California in San Francisco and was introduced in 1956. 'Dixon' trees produced very high yields, which made this variety popular for growers. While 'Dixon' fruit flesh was a desirable yellow-gold, the pit often exhibited a pink to red color from the formation of red anthocyanins. This red color oxidizes to brown when canned, resulting in an undesirable fruit color as well as an undesirable brown staining of canned syrup. The red stained fruit stone or endocarp is also more prone to breakage, resulting in pit fragments being left with the fruit flesh during processing. As a result of these problems, processors stopped purchasing 'Dixon' fruit from growers. Although the 'Dixon' variety is no longer commercially planted, no replacement variety presently exists.

Peach variety 'Andross' was developed as a source of fruit for processors during the early 'Early' maturity season following 'Dixon' production. 'Andross' originated in Davis, Calif., by L. D. Davis, Department of Pomology, University of California, Davis and was introduced in 1964. 'Andross' trees consistently set heavy crops, have leaves with globose glands, and flowers of the larger non-showy type. Although 'Andross' is the most heavily planted variety for the 'Early' maturity season, this variety also produces fruit with red-staining of the pit and associated higher frequencies of endocarp (stone) fragments remaining in processed flesh. Consequently, processors are no longer encouraging new plantings of this variety, and indicate that they may no longer purchase fruit of this variety in the future.

Furthermore, the 'Early' maturity season variety 'Klampt' is not a suitable replacement for 'Andross'. While 'Klampt' fruits and pits are free from red staining, 'Klampt' develops soft fruit soon after ripening, which results in fruit damage during transport and subsequent processing. Consequently, as with 'Andross', processors are no longer encouraging new plantings of 'Klampt', and have indicated that they may no longer purchase fruit of this variety in the future. As a result, there is a need to develop new peach varieties having desirable fruit characteristics, particularly peach varieties having good fruit quality, lacking red staining in the pits, and having pits that resist splitting. The new peach variety 'Vilmos' as described herein is a product of this breeding effort.

SUMMARY OF THE INVENTION

The present disclosure relates to a new and distinct peach cultivar (*Prunus persica*) that has been denominated as 'Vilmos', and more particularly, to such a peach variety that lacks undesirable red staining of the pit in the peach fruit; exhibits low susceptibility to splitting or cracking of the fruit pit during ripening; forms attractive, high quality fruit that matures approximately with, to just after, that of the 'Andross' variety; and demonstrates a capacity to maintain good on-tree fruit firmness and quality for up to 10 days after the initial tree-ripe stage.

'Vilmos' fruit ripens during the commercially important 'Andross' period. In addition to the desirable ripening period of 'Vilmos', this variety produces processing clingstone fruit that remains free from the anthocyanin red pit staining and pit cracking that occurs in 'Andross' while also avoiding the softness-induced fruit damage that occurs during transport (as is present in 'Klampt'). Furthermore, 'Vilmos' demonstrates improved resistance to Peach Flower Blight and Peach Fruit Brown Rot (both caused by *Monilinia* spp.) in lab and field evaluations. The 'Vilmos' peach is a nonmelting, clingstone peach that would be mainly grown and sold as a processing fruit, rather than as a fresh market fruit. The most comparable example of this type of processing clingstone peach is the 'Andross' clingstone peach variety.

'Vilmos' fruit is medium to large in size, slightly angular to round in shape, and has golden-yellow flesh. Following initial ripening, 'Vilmos' demonstrates the capacity to maintain good on-tree fruit quality for up to 10 days, thus allowing delayed harvest, including the more economically efficient single harvests. See also Table 2. The skin of 'Vilmos' fruit is slightly less fuzzy than that of 'Andross' and exhibits a more uniform yellow color. 'Vilmos' pits are medium in size and the tree is upright-spreading with similar vigor to that of 'Andross'. The 'Vilmos' crop is similar to that of 'Andross' and higher than that of 'Carson' (another processing peach variety) under commercial conditions. 'Vilmos' production confers higher processer case yields, as shown in Table 1, Table 3, and Table 4, due to having fewer pit fragments and lacking the red pit staining common to 'Andross'.

Peach variety 'Vilmos' was originally identified from a seedling population obtained from a controlled cross of two peach selections. This cross, which involved the UC processing peach variety 'Loadel' as the female (seed) parent and the UC processing peach breeding line 'F10E6-27' as the male (pollen) parent, the lineages of which are further described in FIG. 2, was made in Year 0. A total of 52 seedlings were recovered from this cross, and these seedlings were subsequently planted in Year 1. The 'Vilmos' seedling, which was given an initial individual seedling designation number of '91,9-161', was grown along with many other seedlings in a Peach Seedling Evaluation Block at the University of California at Davis starting in Year 1. Fruit from the original '91,9-161' seedling was first evaluated in Year 4, with continued canned sample evaluations from Years 5 to 25.

The original '91,9-161' ('Vilmos') tree was first asexually reproduced in Davis, Calif. via T-budding propagation onto 'Lovell' peach rootstock in Year 6 and has been maintained in an advanced selection block at the Wolfskill Experimental Orchards in Winters, Calif. since that time. In Year 11, '91,9-161' was selected based on its good fruit and tree qualities, its freedom from red staining of the pit, and its desirable 'Andross' ripening time. In Year 11, '91,9-161' was propagated and placed into regional test plantings at the Wolfskill Experimental Orchards, at the Davis Pomology Field Facilities, and at the Kearney Agricultural Center in Parlier, Calif. All propagated trees of this new variety produced fruit during the Year 14 growing season. All fruit were true-to-type to the original seedling. From Years 15 to 25, additional grower evaluation plots were established for this selection in the Sacramento and San Joaquin Valleys of California under the individual seedling designation of 'Early #5'. Selection '91,9-161' was chosen as a candidate for release under the variety name 'Vilmos'.

Field test evaluations through Year 25 have been successful at demonstrating the desirable characteristics of 'Vilmos'. Tree-ripe fruit of this variety demonstrates the capacity to maintain good quality for over one week on the tree, allowing delayed and economically efficient once-over harvests, rather than the multiple harvests practiced for most current varieties. Furthermore, 'Vilmos' has demonstrated improved resistance to Peach Flower Blight and Peach Fruit Brown Rot (both caused by *Monilinia* spp.) in lab- and field-based evaluations. No serious disease or pest damage from other sources has been observed during the evaluation period when standard commercial practices are followed.

BOTANICAL DESCRIPTION OF THE PLANT

The following is a detailed horticultural description of the new peach cultivar 'Vilmos' obtained from vegetatively-propagated trees observed during the Year 20 through Year 25 growing seasons. The trees were planted in Year 11 and grown at the Wolfskill Experimental Orchards of the University of California located at Winters, Calif. Color designations are presented with reference to the "Dictionary of Color" by Maerz and Paul, First Edition (1930). Unless otherwise noted, trees described in this section were 14 to 15 years old ($13^{th}$ to $14^{th}$ leaf or years after field planting). Reference to standard commercial conditions herein generally refers to standard commercial orchard conditions of training, pruning, and thinning.

Botanical classification: *Prunus persica*, cv. 'Vilmos'.

Tree:

*Size*.—Medium. The height of the tree (at 24 years old) is approximately 3.8 m and the breadth of the tree is approximately 3.6 m across the crown when commercially trained to four scaffolds.

*Vigor*.—Medium.

*Growth*.—Upright-spreading.

*Hardiness*.—Hardy under typical Sacramento Valley climatic conditions.

*Production*.—Productive.

*Bearing*.—Regular bearer. Bearing is on long shoots only.

Figure 4:
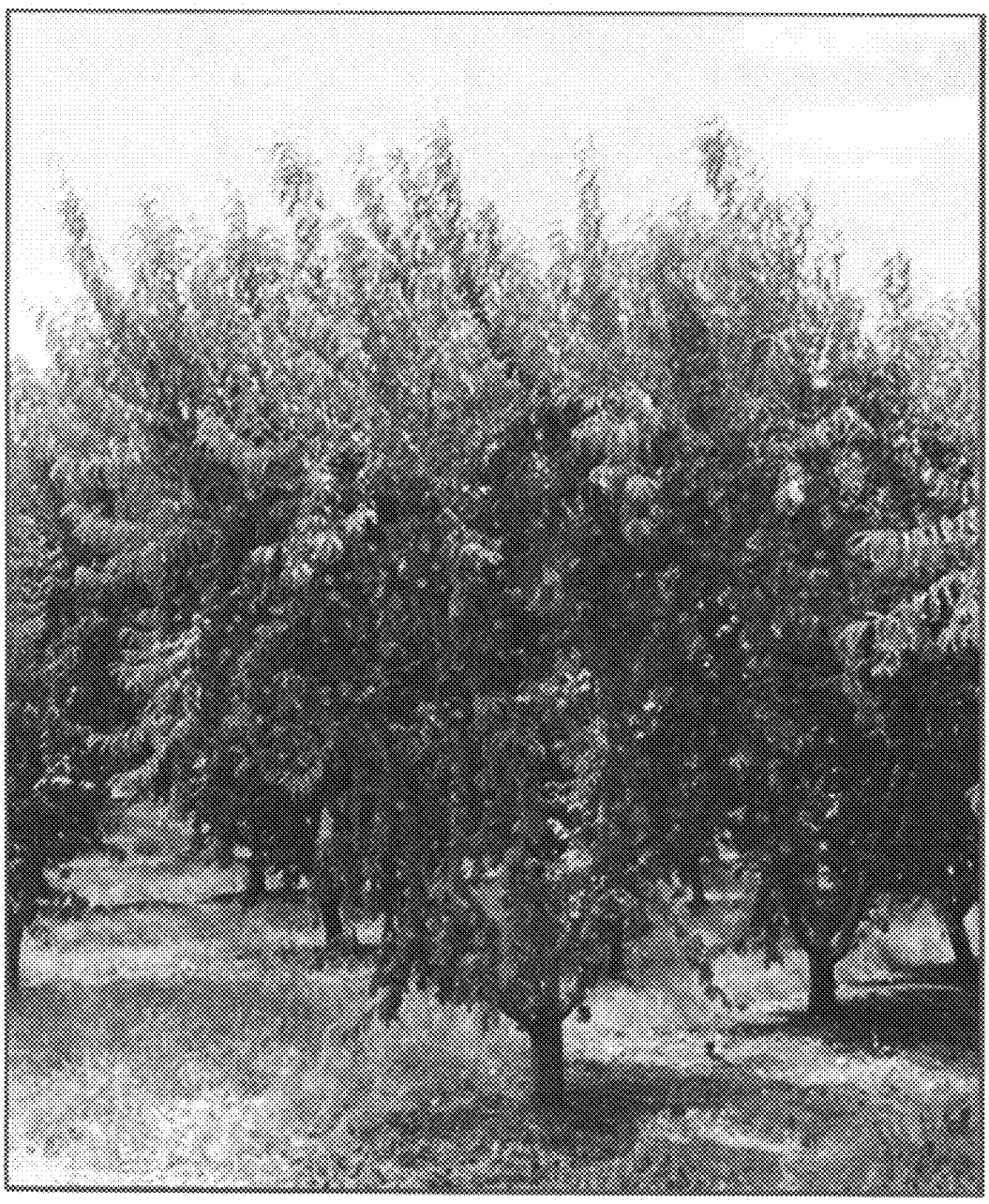
FIG. 4 illustrates a 'Vilmos' tree in a production plot bearing fruit.

Trunk:

*Size*.—Medium to large. The diameter of the trunk 10 cm above the ground is approximately 22-25 cm in 14-year-old trees. The scaffold diameters at the base of the scaffolds are approximately 15 cm. An image of a 6-year-old 'Vilmos' tree under commercial production (Table 3) is presented in FIG. 4.

*Texture*.—Relatively coarse, with substantial scarfskin.

*Color*.—Bark color ranges from light-grey (14-A-2) to dark grey (7-C-7).

*Lenticels*.—Numerous, medium, flattened, and generally oval-shaped. Typically the lenticels range from approximately 4-6 mm wide, are at right angles to the trunk, and are approximately 1-2 mm tall. The color of the lenticel surface is light brown (13-J-9).

Branches:

*Size*.—Medium. The diameter of branches at 2 m above the ground is approximately 12.7 cm.

*Texture*.—Medium.

*Color*.—Mature shoots are light grey (14-A-2) to medium brown (7-C-8). The current season's shoots are pale light green (20-L-6). The exposed surfaces are commonly tinged rose-red (17-H-3). The color of the new expanding shoot tips is bright yellow green (20-L-6).

*Lenticels*.—At a right angle to the shoots. The lenticel surface is light brown (13-J-11 Sorrel) in coloration and is moderately calloused.

*Internode length*.—On current season's hanger shoots, the length between nodes is commonly approximately 20-30 mm.

*Spurs*.—Spurs are not produced under commercial conditions.

*Vegetative buds*.—The vegetative bud size is approximately 5 mm in length and 3 mm in width. Vegetative buds are acute in shape. The position of vegetative buds is slightly held out in relation to 1-year-old shoots at the final stages of dormancy.

Leaves:

*Size*.—Medium to large. Typical length from vigorous current season's growth is approximately 16-19 cm (including the petiole) and typical width is approximately 4-5 cm.

*Thickness*.—Average. The leaf thickness is approximately 2 mm.

*Form*.—Lanceolate.

*Apex*.—Acuminate and often with slight curves downward.

*Aspect*.—The blade commonly ranges from substantially flat to somewhat folded upwards.

*Color*.—The upper surface is dark green (23-L-4), and the lower surface is a much lighter grey-green (21-J-6). The primary vein and mid-vein on the under surface is pale yellow-green (17-H-1).

*Margin*.—Crenate and occasionally double crenate. The crenations are relatively large and uniform. The leaf margins commonly range from straight to moderately undulate.

*Petiole*.—Generally medium in size, commonly approximately 8 to 16 mm in length, approximately 2 mm in thickness, and pale yellow-green in coloration (17-J-4).

*Glands*.—Small to medium in size, almost always globose, and alternate. The gland diameter is approximately 1.7 mm. There are commonly 1-3 glands on a petiole, and frequently 0-3 additional glands can be observed at the base of the leaf blade. The coloration is shiny light green-yellow (17-K-6), occasionally developing a reddish tinge with age.

*Stipules*.—Linear lanceolate in configuration. Most stipules are early deciduous, their margins are serrate, and they are commonly approximately 6-9 mm long. The color of young stipules is commonly light green-yellow (17-K-5), with darkening to brownish upon aging.

Fruit:

*Maturity when described*.—Full commercial maturity.

*Picking*.—In Year 23 (a typical year), fruit was first picked on July 19 and last picked on July 31.

*Season of maturity*.—Approximately with, to just after, the 'Andross' variety.

Figure 3:
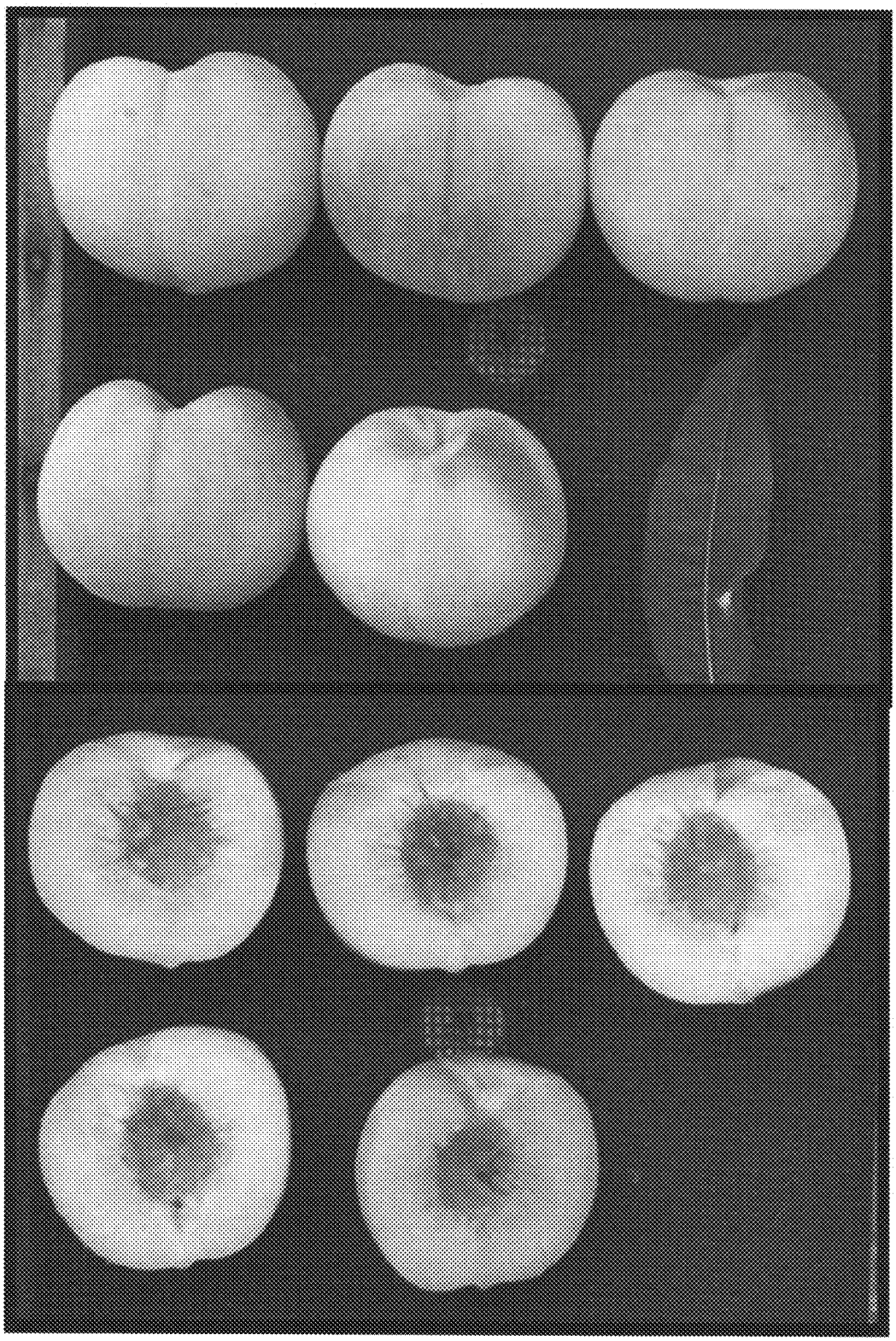
FIG. 3 illustrates (top) whole ripe 'Vilmos' peaches with a typical mature leaf, and (bottom) halves of 'Vilmos' peaches following cutting in a standard commercial torque pitter.

*Size*.—Uniform and large. The average axial diameter of highly thinned fruit is approximately 60 cm, the average suture diameter is approximately 70 cm, and the average cheek diameter is approximately 68 cm. See also Table 1. Images of 'Vilmos' fruit are also presented in FIG. 3.

*Form*.—In lateral aspect, the fruit is slightly oblate in form. In apical aspect, the fruit is nearly globose, with slight variability. Most frequently, the fruit is slightly asymmetrical.

*Suture*.—Inconspicuous line, often slightly deeper at the base, with a slight depression at the pistil.

*Ventral surface*.—Relatively smooth, and only occasionally lipped.

*Base*.—Rounded to slightly truncate in form. The angle of the base is slightly variable, but most often it is at a right angle to the fruit axes.

*Stem cavity*.—Broad, and moderately deep. The average length is approximately 3 cm, the average width is approximately 2 cm, and the average depth is approximately 1.5-2 cm.

*Apex*.—Generally rounded, with a slight tip.

*Pistil point*.—Most frequently it is oblique.

*Stem length*.—Medium in length, averaging approximately 8 mm.

*Stem thickness*.—Commonly approximately 3 mm, and usually more thickened at the distal end.

*Skin pubescence*.—Pubescent with a fine, short, matted pubescence. No observed tendency to crack.

*Skin color*.—The primary ground color is a uniform orange-yellow (9-L-3). The fruit surface has a moderate amount of red blush coloration present on 20-50% of the total surface. Fruits exposed to direct sunlight are usually in the highest percent category. The blush pattern is primarily washed, with some mottling present. The blush color ranges from a dark garnet red (7-H-4) to a lighter shade of red (6-K-7), with a range of variation in between. Lenticels are not visible on the fruit.

*Flesh color*.—A uniform yellow from skin to stone cavity (10-L-3).

*Flesh texture*.—Fine and non-melting.

*Flesh fibers*.—Few in number; short and fine.

*Ripening*.—Ripens evenly.

*Flavor*.—Fruit develops excellent quality, rich in flavor and well-balanced. Flavor was rated as superior to that of 'Andross' in taste trials. The typical fruit acidity is 0.55 total titratable acidity. The typical fruit sweetness is 11.50 Brix (See Table 1).

*Aroma*.—Moderate, pleasant.

*Eating quality*.—Good.

*Canning quality*.—Very good.

*Fruit firmness*.—The typical fruit firmness is 7.2 pounds.

*Fruit juiciness*.—The typical fruit juiciness is 0.16 dry weight/fresh weight (dry weight is 16% that of the fresh weight).

*Stone type*.—Clingstone, with flesh connected over the entire stone surface. The fruit adherence of stone to flesh is strong.

*Stone size*.—Medium to slightly below average. The average length is approximately 35 mm, the average width is approximately 28 mm, and the average thickness is approximately 22 mm.

*Stone form*.—Fine fibers are present, being numerous, very short, and attached laterally to the stone.

*Form*.—Variable, but most often slightly obovate.

*Stone base*.—Typically positioned at right angles to, or slightly oblique to, the stone axis.

*Stone hilum*.—Medium to small in size, and well-defined. The hilum length is typically 6-7 mm and the hilum width is 5 mm. The hilum is surrounded by a raised collar.

*Apex*.—Apex form is generally rounded with a medium, blunt tip. The tip length is typically 4 mm in length and 3-4 mm in width.

*Stone side*.—Variable, but typically longer on ventral side.

*Stone surface*.—Moderately coarse, with the heaviest grooving apically over the lateral apical shoulders. Several deep grooves are present near the dorsal and ventral edge, meeting the edge at an oblique angle.

*Ventral edge*.—Medium in width, with several low wings. The ventral edge width is approximately 4 mm.

*Dorsal edge*.—Somewhat variable in form, but most often the dorsal suture is moderately thick, with a deep groove present from the base up to the apical shoulder. The apical shoulder area is somewhat eroded and somewhat concave in shape. The dorsal groove is bordered by two high ridges.

*Stone color*.—When dry, light clay-brown (13-C-8).

*Tendency to split*.—Low.

Flowers:

*Chilling season*.—Low to medium for growing location. Good commercial crops were achieved with chilling hours below 45° F., and accumulated between November 1 and January 26, ranging from 500 to 900 hours for the Years 20-25 evaluation period.

*Buds*.—Medium size, conic in form, plump, free slight (4-8 mm) stem, with moderate pubescent surfaces with light grey colorations. Typical flower bud length is approximately 9-12 mm and flower bud width is 6-8 mm at the pink-tip stage. The color of the exterior bud scale ranges from grey (8-J-6) to mocha- brown (15-J-5). The buds are hardy under typical climatic conditions of the Sacramento Valley. There are usually one or, more frequently, two floral buds per node.

*Bloom timing*.—Mid-season in relation to other commercial cling peach cultivars. Bloom periods were approximately similar to 'Andross' during the evaluation period.

Figure 1:
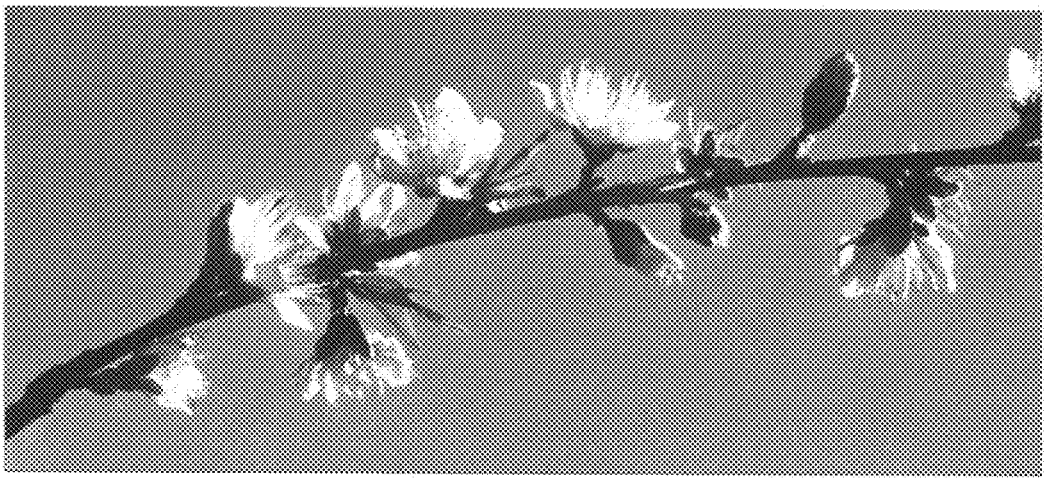
FIG. 1 illustrates flowers of 'Vilmos', including open, non-showy type flowers and closed flower buds.
Figure 2:
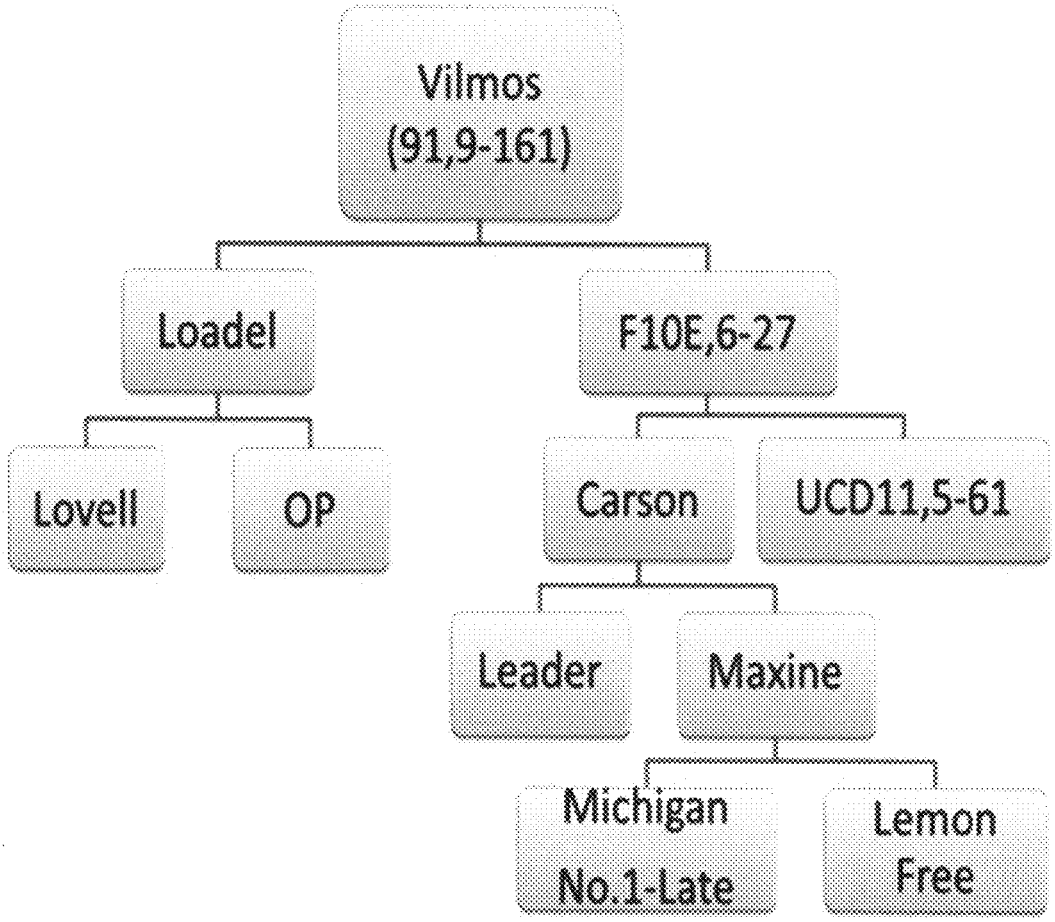
FIG. 2 illustrates the lineage of 'Vilmos', with progeny displayed above their respective parents.

*Size*.—As shown in FIG. 1, the flower is non-showy, and medium in size. The fully expanded flower diameter is approximately 22-30 mm.

*Bloom quality*.—Commonly abundant throughout the tree.

*Petals*.—Medium; commonly approximately 12-16 mm long and approximately 10-16 mm wide. The petal number is five. Petal form varies from broadly ovate to nearly oval. Petal color is very light pink (1-D-1). The petal claw is medium and truncate in form. Claw color is a dark pink (2-1-5). Petal margins are moderately undulate, and the petals are substantially cupped inward. The petal apices are usually rounded, with no tip. The flower arrangement of petals is free except at the base where there is slight overlap.

*Flower pedicel*.—Medium; commonly 4-8 mm in length with an average thickness of approximately 2 mm. Pedicel color is a light green (17-K-6). Pedicel surface is glabrous.

*Nectaries*.—Moderately bright orange (9-C-12) at maturity.

*Anthers*.—Average in size, typically 0.5-1.0 mm. Anther color is almost white (14-L-1) at dehiscence to maroon (4-K-7) by petal fall. Anthers are located internally to the petals, and are attached at the edge of the floral cup.

*Pollen*.—Abundant. Pollen color is a bright yellow-gold (10-L-7).

*Stamens*.—Medium length and slightly longer than the pistil at full maturity. Typical stamen length is approximately 14.6 mm. Filament color is nearly white (1-B-1) when the flower first opens, darkening to a dull light violet (4-H-3) with senescence.

*Calyx*.—Glabrous and quite rugose, and the coloration is light maroon (7-L-9) at maturity.

*Sepals*.—Greyish pubescent, average in size, conic in form, and red-brown (7-H-11 to 6-J-5) in color. Typical sepal length is approximately 6-8 mm and sepal width is 4-6 mm at flowering.

*Pistil*.—Pubescent basally over the ovary, being less so near the stigma and over the upper style area. Pistils are commonly approximately 12-18 mm in length, including the ovary. The coloration is pale green (17-J-3) basally, and a paler green (17-E-2) over the upper style area.

*Fertility*.—'Vilmos' is fully self-fertile.

Figure 5:
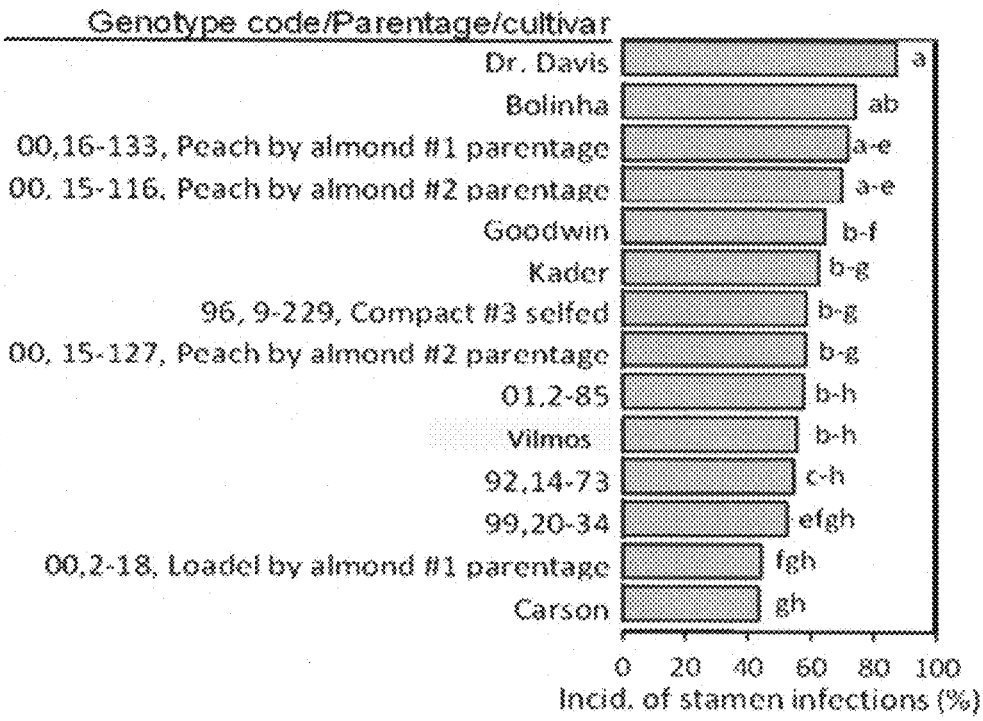
FIG. 5 illustrates flower blight resistance rating results from controlled lab testing on 14 peach varieties, including 'Vilmos', standard processing peach cultivars, and advanced breeding lines. Closed blossoms were collected in the field, allowed to open under controlled laboratory conditions, and inoculated with conidia of *Monilinia fructicola* at 20K/mL. Blossoms were evaluated for stamen infections after 5-6 days of incubation at 20° C.

Major use: Canning.
Keeping quality: Good.
Resistance to insects and diseases: Low to medium susceptibility to *Monilinia* fruit brown rot and flower blight, otherwise average. See also FIG. 5 and Table 5.

COMPARISONS TO OTHER PEACH VARIETIES

The tables below provide quantitative analyses of various phenotypic attributes of 'Vilmos' and other varieties. Phenotypes analyzed include e.g. fruit quality data, yield reports, and resistance ratings to fruit brown-rot (*Monilinia fructicola*).

When compared to male parental variety 'F10E6-27', 'Vilmos' fruit has comparable stone adhesion, flesh and ground color, but produces a larger and firmer fruit at maturity.

Table 1 below shows fruit quality data averaged over the 3 years of the RosBreed-1 evaluations for 'Vilmos' and standard commercial cultivars in the 'Extra-Early' and 'Early' harvest seasons. Flowers were heavily thinned to 18-24 inches between developing fruit in order to maximize potential fruit size and quality.

TABLE 1

| Selection | Red stain in pit cavity | Pit fragments | Blush | CIELAB color - a* | Harvest |
|---|---|---|---|---|---|
| Loadel | No | No | Very Light | 5.65 | Jul. 16 |
| Carson | No | No | Very Light | 4.97 | Jul. 23 |
| Dee-Six | No | No | Very Light | 8.07 | Jul. 29 |
| Kader | No | No | Moderate | 6.98 | Jul. 29 |
| Dixon | Yes | Yes | Moderate | 6.07 | Jul. 29 |
| Goodwin | Yes | Yes | Light | 9.07 | Aug. 3 |
| Andross | Yes | Yes | Light | 6.87 | Aug. 10 |
| Vilmos | No | No | Light | 11.99 | Aug. 11 |
| Klampt | No | No | Very Light | 5.43 | Aug. 12 |
| Ross | No | No | Moderate | 5.27 | Aug. 13 |
| Dr. Davis | No | No | Light | 7.17 | Aug. 19 |

| Selection | pH | Brix | Brix/TA | TA | Fruit width (mm) | Fruit length (mm) |
|---|---|---|---|---|---|---|
| Loadel | 3.85 | 8.00 | 16.81 | 0.48 | 671.38 | 684.94 |
| Carson | 4.04 | 7.50 | 17.05 | 0.44 | 583.69 | 548.64 |
| Dee-Six | 4.14 | 10.00 | 22.32 | 0.45 | 651.75 | 669.41 |
| Kader | 3.98 | 12.50 | 25.67 | 0.49 | 723.77 | 657.67 |
| Dixon | 4.06 | 12.30 | 30.22 | 0.41 | 769.97 | 763.35 |
| Goodwin | 3.85 | 12.70 | 22.56 | 0.56 | 728.08 | 706.53 |
| Andross | 4.09 | 12.40 | 30.54 | 0.41 | 788.19 | 784.22 |
| Vilmos | 3.77 | 11.50 | 20.80 | 0.55 | 709.42 | 583.21 |
| Klampt | 3.87 | 10.70 | 21.57 | 0.50 | 830.48 | 874.03 |
| Ross | 3.82 | 10.80 | 22.45 | 0.48 | 719.72 | 707.10 |
| Dr. Davis | 3.85 | 11.80 | 22.35 | 0.53 | 743.07 | 740.33 |

| Selection | Fruit cheek width (mm) | Fruit weight (g) | Flesh firmness (lbs.) |
|---|---|---|---|
| Loadel | 643.38 | 183.74 | 8.3 |
| Carson | 580.25 | 219.48 | 8.2 |
| Dee-Six | 617.09 | 226.82 | 7.3 |
| Kader | 659.26 | 332.74 | 7.2 |
| Dixon | 719.71 | 226.42 | 5.6 |
| Goodwin | 720.79 | 236.20 | 9.4 |
| Andross | 674.54 | 332.22 | 6.5 |
| Vilmos | 669.15 | 235.68 | 7.2 |
| Klampt | 704.69 | 353.12 | 5.9 |
| Ross | 645.08 | 236.02 | 9.2 |
| Dr. Davis | 729.54 | 320.00 | 8.2 |

Table 2 below shows average fruit firmness for 'Andross', 'Vilmos', and 'Klampt' processing peaches when harvested at the tree ripe stage, and again at 2 and 4 weeks after the initial tree ripe date. Data are from Year 25 trees grown under standard commercial conditions.

TABLE 2

| | | Fruit Firmness in pounds {Standard Deviation} | | |
|---|---|---|---|---|
| | Ripe Date (Year 25) | Tree-Ripe | 2 weeks after Tree-ripe | 4 weeks after Tree-ripe |
| 'Andross' | Jul. 15 | 5.8 {1.5} | 2.4 {1.3} | <1.0 |
| 'Vilmos' | Jul. 16 | 6.4 {1.2} | 5.4 {1.8} | 4.5 {2.6} |
| 'Klampt' | Jul. 18 | 6.3 {1.8} | <1.0 | <1.0 |

Table 3 below shows comparative yields for 'Vilmos' and 'Andross' processing peaches grown under standard commercial conditions in the Live Oak, Calif. grower evaluation trial during Years 20-25. Yields are for commercially acceptable fruit after removal of undersized and damaged fruit at grading station.

TABLE 3

| Year | 'Vilmos' (lbs.) | 'Andross' (lbs.) |
|---|---|---|
| 20 | 63700 | 118140 |
| 21 | 122500 | 114840 |
| 22 | 112700 | 116160 |
| 23 | 117600 | 120780 |
| 24 | 130340 | 123420 |
| 25 | 134260 | 126720 |

Table 4 below shows comparative yields for 'Vilmos' and 'Andross' processing peaches grown under standard commercial conditions in the Year 25 Linden, Calif. grower evaluation trials. 'Andross' trees were thinned to standard commercial practices, while one block of 'Vilmos' was thinned to standard commercial practices (800-1000 fruit/tree) and a second block of 'Vilmos' was lightly thinned (1200-1400 fruit/tree), demonstrating the ability of 'Vilmos' to effectively size fruit, even if over-cropped. Yields are for commercially acceptable fruit after removal of undersized and damaged fruit at grading station.

TABLE 4

| Treatment | Yield (Tons/Acre) |
|---|---|
| 'Andross': Standard thin | 17.2 |
| 'Vilmos': Standard thin | 17.5 |
| 'Vilmos': Light thin | 20.4 |

Table 5 below shows fruit brown-rot (*Monilinia fructicola*) resistance ratings from controlled lab testing on various peach varieties. Severity rating is the product of lesion incidence by average lesion diameter 48 hours after controlled inoculation. Data shown are averages of results from Years 19, 20, and 21.

TABLE 5

| Selection | Average Brown-Rot Severity | Standard Deviation |
|---|---|---|
| 'Carson' | 13.19 | 6.10 |
| 'Kader' | 3.11 | 2.89 |
| 'Vilmos' | 6.39 | 6.19 |
| 'Goodwin' | 5.83 | 4.98 |
| 'Ross' | 21.28 | 7.01 |

What is claimed is:

1. A new and distinct variety of peach tree designated 'Vilmos' as shown and described herein.

* * * * *